United States Patent [19]
Kato et al.

[11] Patent Number: 5,856,868
[45] Date of Patent: Jan. 5, 1999

[54] FOREIGN SUBSTANCE INSPECTING APPARATUS AND METHOD THEREOF

[75] Inventors: Kinya Kato, Yokohama; Yumi Nakagawa, Kawasaki, both of Japan

[73] Assignee: Nikon Corporation, Tokyo, Japan

[21] Appl. No.: 889,558

[22] Filed: Jul. 8, 1997

[30] Foreign Application Priority Data

Jul. 9, 1996 [JP] Japan .................................... 8-198306
Jul. 9, 1996 [JP] Japan .................................... 8-198307

[51] Int. Cl.$^6$ ................................................. G01N 21/88
[52] U.S. Cl. ............................................................ 356/237
[58] Field of Search .................................... 356/237, 431; 250/559.41

[56] References Cited

U.S. PATENT DOCUMENTS

| | | |
|---|---|---|
| 4,468,120 | 8/1984 | Tanimoto et al. ................ 356/237 |
| 5,017,798 | 5/1991 | Murakami et al. ............ 250/559.41 |
| 5,528,360 | 6/1996 | Kohno .............................. 356/237 |

*Primary Examiner*—Richard A. Rosenberger
*Attorney, Agent, or Firm*—Morgan, Lewis & Bockius LLP

[57] ABSTRACT

A foreign substance inspecting apparatus and method for detecting a foreign substance on a surface, includes a light source for providing light; a plurality of condensing optical systems for collecting the light from the light source and for forming a plurality of light spots on the surface; a scanning system for scanning the surface using the light spots formed by the condensing optical systems; a detecting optical system for detecting light scattered from at least one of the light spots by the foreign substance on the surface; and a surface shape measuring system for measuring a shape of the surface, wherein a focus of each one of the condensing optical systems is individually adjusted according to the surface shape measured by the surface shape measuring system.

17 Claims, 8 Drawing Sheets

FOREIGN SUBSTANCE INSPECTING APPARATUS AND METHOD THEREOF

This application claims the benefit of Application Nos. 08-198306 filed in Japan on Jul. 9, 1996 and 08-198307 filed in Japan on Jul. 9, 1996, which are hereby incorporated by reference.

BACKGROUND OF THE INVENTION

1. Field of the Invention

The present invention relates to an apparatus for inspecting whether foreign substances are adhered to a surface, and more particularly, to an apparatus used in the process of manufacturing semiconductor devices, liquid crystal display devices or the like.

2. Related Background Art

In the process of manufacturing liquid crystal display devices, for example, a pattern formed on a photomask (hereafter referred to as a "mask") is projected and exposed on a plate used as a photosensitive substrate. When a foreign substance, such as small debris, adheres to the mask during projection exposure, the image of the foreign substance is transferred to the plate along with the pattern image, thereby creating defects in the pattern. Accordingly, inspection for the presence and position of foreign substances on the mask using a foreign substance inspecting apparatus is necessary prior to projection exposure.

In particular, since the size of liquid crystal substrates has significantly increased, it is necessary to inspect for foreign substance over an area of a large substrate. With the foreign substance inspecting apparatus disclosed in Japanese Laid-Open Patent Publication 8-29353, a beam spot scans one direction on the inspected surface using one scanning lens having a wide scanning region. Furthermore, detection of foreign substances is accomplished using the scattered light from the foreign substances with respect to the beam spot while moving the inspected surface in a direction orthogonal to the scanning direction of the beam spot.

As described above, when the scanning region of the scanning lens becomes about 500 mm, for example, accompanying the increase in size of the substrate, the required diameter of the scanning lens becomes about 150 mm. As a result, production costs for the scanning lens increase greatly, and the apparatus as a whole becomes bulkier. In addition, when the substrate is not flat, focussing of the scanning lens over the entirety of a wide scanning region is difficult, so that the sensitivity in detecting foreign substances varies depending on the detection position.

In another process of manufacturing circuit patterns for liquid crystal display devices or semiconductor devices, a pattern formed on a mask is projected and exposed on a photosensitive substrate. When a foreign substance, such as small debris, adheres particularly to the pattern surface of the mask during projection exposure, the image of this foreign substance is transferred to the photosensitive substrate, thereby creating defects in the pattern. Consequently, a pellicle membrane is often provided on the pattern surface side of the mask to prevent foreign substances from adhering to the pattern surface of the mask. In this case, the effects of transferring foreign substances adhered to the pellicle membrane are a great deal smaller than the effects of transferring foreign substances adhered to the pattern surface of the mask. However, when the foreign substance adhered to the pellicle membrane has a certain size, the image of this foreign substance is transferred to the photosensitive substrate. In addition, when a foreign substance of a certain size is adhered to the back surface (the glass surface on the side opposite the pattern surface) of the mask, the image of this foreign substance is also transferred to the photosensitive substrate.

Hence, a foreign substance inspecting apparatus for inspecting foreign substances adhered to the mask and the pellicle membrane has been proposed. In the conventional foreign substance inspecting apparatus, the inspected surface is scanned by one beam spot formed by one scanning optical system using a beam with strong directivity, such as a laser beam. Furthermore, the scattered light, with respect to the beam spot, from the foreign substance on the inspected surface is detected by a light-receiving optical system.

However, when the size of the mask becomes large, the required scanning range also becomes wide. Consequently, there are many cases where the focal length of the scanning lens in the scanning optical system is lengthened. In this case, because the separation between the scanning lens and the inspected surface is also lengthened, the diameter of the scanning lens and the size of other optical components, such as bending mirrors between the scanning lens and the inspected surface, also become larger. As a result, production costs of components such as the scanning lens increase, and the apparatus becomes bulkier.

In addition, with regard to the light-receiving optical system, because it is necessary to have a wide scanning range with the same numerical aperture (NA), the diameter of the light-receiving lens and the size of other optical components increase. As a result, production costs for components such as the light-receiving lens increase, and the apparatus as a whole becomes bulkier.

Furthermore, with the conventional technology, a glass material is used as the light-absorbing member for absorbing the mirror reflected light of the beam spot. Accordingly, as the size of the mask increases and the scanning range widens, it is necessary to maintain the length for covering the scanning range as a whole by adhering a plurality of glass members together. However, when light is incident on the adhesion region between adjacent glass members, the light is not absorbed but scattered, thereby enabling scattered light to enter the light-receiving optical system as stray light.

SUMMARY OF THE INVENTION

Accordingly, the present invention is directed to a foreign substance inspecting apparatus that substantially obviates one or more of the problems due to limitations and disadvantages of the related art.

An object of the present invention is to provide a compact foreign substance inspecting apparatus capable of detecting foreign substances with the required detection sensitivity for a large surface.

Another object of the present invention is to provide a small foreign substance inspecting apparatus capable of detecting foreign substances with high accuracy over a large surface.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the foreign substance inspecting apparatus for detecting a foreign substance on a surface includes a light source for providing light; a plurality of condensing optical systems for collecting the light from the light source and for forming a plurality of light spots on the surface; a scanning system for scanning the surface using the light spots formed by the condensing optical systems; a detecting optical system for detecting light scattered from at least one of the light spots by the foreign substance on the surface; and a surface shape measuring system for measuring a shape of the surface, wherein a focus of each one of the condensing optical systems is individually adjusted according to the surface shape measured by the surface shape measuring system.

In another aspect, the foreign substance inspecting apparatus, for scanning a surface using a light spot to detect the presence of a foreign substance according to light scattered from the light spot by the foreign substance, includes a plurality of scanning optical systems for forming light spots on the surface and for scanning the surface using the light spots; a plurality of light-receiving optical systems for receiving the light scattered from the light spots by the foreign substance; and a light absorbing member for absorbing mirror reflected light from the light spots.

In another aspect, the method for detecting the presence of a foreign substance on a surface includes the steps of providing light from a light source; collecting the light from the light source using a plurality of condensing optical systems; forming a plurality of light spots on the surface from the light collected by the plurality of condensing optical systems; scanning the surface using the light spots formed by the condensing optical systems; detecting light scattered by the foreign substance on the surface from at least one of the light spots; measuring a shape of the surface; and individually adjusting a focus of each one of the condensing optical systems according to the measured surface shape.

To further achieve the advantages and in accordance with the purpose of the present invention, as embodied and broadly described, the foreign substance inspecting apparatus includes a plurality of condensing optical systems for collecting the light rays from a light source and forming small light spots on a surface being inspected; a scanning system for scanning the surface being inspected using the plurality of light spots formed by the plurality of condensing optical systems; a detecting optical system for detecting a foreign substance on the basis of scattered light from the foreign substance on the surface being inspected with respect to the plurality of light spots; and a surface shape measuring system for measuring the surface shape of the surface being inspected; wherein the focus of each condensing optical system is adjusted individually on the basis of the surface shape of the surface being inspected that has been measured by the surface shape measuring system.

Preferably, the scanning system has plurality of scanning optical systems for causing each of the plurality of light spots formed by the plurality of condensing optical systems to move along a first direction, and a movement system for causing the surface being inspected to move along a second direction orthogonal to the first direction in the surface being inspected; the detecting optical system has a plurality of light-receiving optical systems for receiving the scattered light from the foreign substance on the surface being inspected with respect to each of the plurality of light spots; and the scanning loci of the plurality of light spots along the first direction in the surface being inspected are mutually separated along the second direction by the plurality of scanning optical systems. In this case, each of the scanning optical systems is preferably a moving mirror provided on the optical path between the light source and the corresponding condensing optical system out of the plurality of condensing optical systems.

In addition, bending mirrors may be provided on the optical paths between the surface being inspected and each of the plurality of condensing optical systems; and the plurality of bending mirrors may be each caused to move parallel so that the intersections between the surface being inspected and the optical axis of each of the plurality of light-receiving optical systems are positioned on the corresponding scanning loci out of the scanning loci of the plurality of light spots obtained on the surface being inspected. The surface shape measuring system has a light-receiving system for receiving the mirror reflected light of at least one light spot out of the plurality of light spots, and measures the surface position of the surface being inspected on the basis of the light-receiving position of the mirror reflected light.

In another aspect, the foreign substance inspecting apparatus includes a plurality of scanning optical systems for forming light spots on the surface being inspected and scanning the surface being inspected using these formed light spots; a plurality of light-receiving optical systems for receiving the scattered light from the foreign substance with respect to the plurality of light spots formed on the surface being inspected by the plurality of scanning optical systems; and a light absorbing member for absorbing the mirror reflected light from the plurality of light spots formed on the surface being inspected.

Preferably, the light absorbing member is made of an organic material for absorbing light having a specific wavelength, or an organic material containing a pigment for absorbing light having a specific wavelength. In this case, it is preferable for the material to be plastic, and more particularly acrylic resin.

It is to be understood that both the foregoing general description and the following detailed description are exemplary and explanatory and are intended to provide further explanation of the invention as claimed.

BRIEF DESCRIPTION OF DRAWINGS

The accompanying drawings, which are included to provide a further understanding of the invention and are incorporated in and constitute a part of this specification, illustrate embodiments of the invention and together with the description serve to explain the principles of the invention. In the drawings.

DESCRIPTION OF THE PREFERRED EMBODIMENTS

Reference will now be made in detail to the preferred embodiments of the present invention, examples of which are illustrated in the accompanying drawings.

In a first embodiment, a plurality of very small light spots are formed on the inspected surface by a plurality of condensing optical systems. Furthermore, foreign substances are detected on the basis of the scattered light from the foreign substances while the inspected surface is scanned by the plurality of light spots. In addition, the focus of each of the condensing optical systems is adjusted, for example by causing the scanning lens of each of the condensing optical systems to move along the optical axis on the basis of the surface shape of the inspected surface measured by the surface shape measuring system.

In this way, with the first embodiment, a plurality of very small light spots are formed on the inspected surface by a plurality of condensing optical systems. Consequently, the required scanning region of each condensing optical system for a large surface becomes smaller. As a result, the required diameter of the scanning lens of each condensing optical system becomes smaller, thereby realizing a reduction in production costs for the scanning lenses and a compactness in the apparatus.

In addition, with the first embodiment, the focus of each condensing optical system may be adjusted separately according to the surface shape of the inspected surface, even when there are undulations, slopes, or other non-flat regions in the surface. As a result, foreign substance detection with sufficient detection sensitivity is achieved over a large surface.

With the specific configuration, for example through the operation of a scanning optical system such as a moving mirror, each of the plurality of light spots formed by the plurality of condensing optical systems is caused to move along a first direction, and a plurality of scanning loci are formed along the first direction. Furthermore, through the operation of a motion means, such as a motion stage for example, the inspected surface moves along a second direction orthogonal to the first direction on the inspected surface. Thus, two-dimensional scanning of the surface is achieved by forming the plurality of scanning loci and moving the inspected surface.

In addition, the scattered light from foreign substances on the inspected surface to each of the plurality of light spots is received by the respective plurality of light-receiving optical systems. Hence, the scanning loci of the plurality of light spots along the first direction obtained on the inspected surface are preferably mutually separated along the second direction. As a result, the scattered light with respect to the light spots formed by each of the condensing optical systems is received with certainty by the corresponding light-receiving optical system. That is, in each light-receiving optical system, scattered light from a light spot other than the corresponding light spot are prevented from being received.

Figure 1:
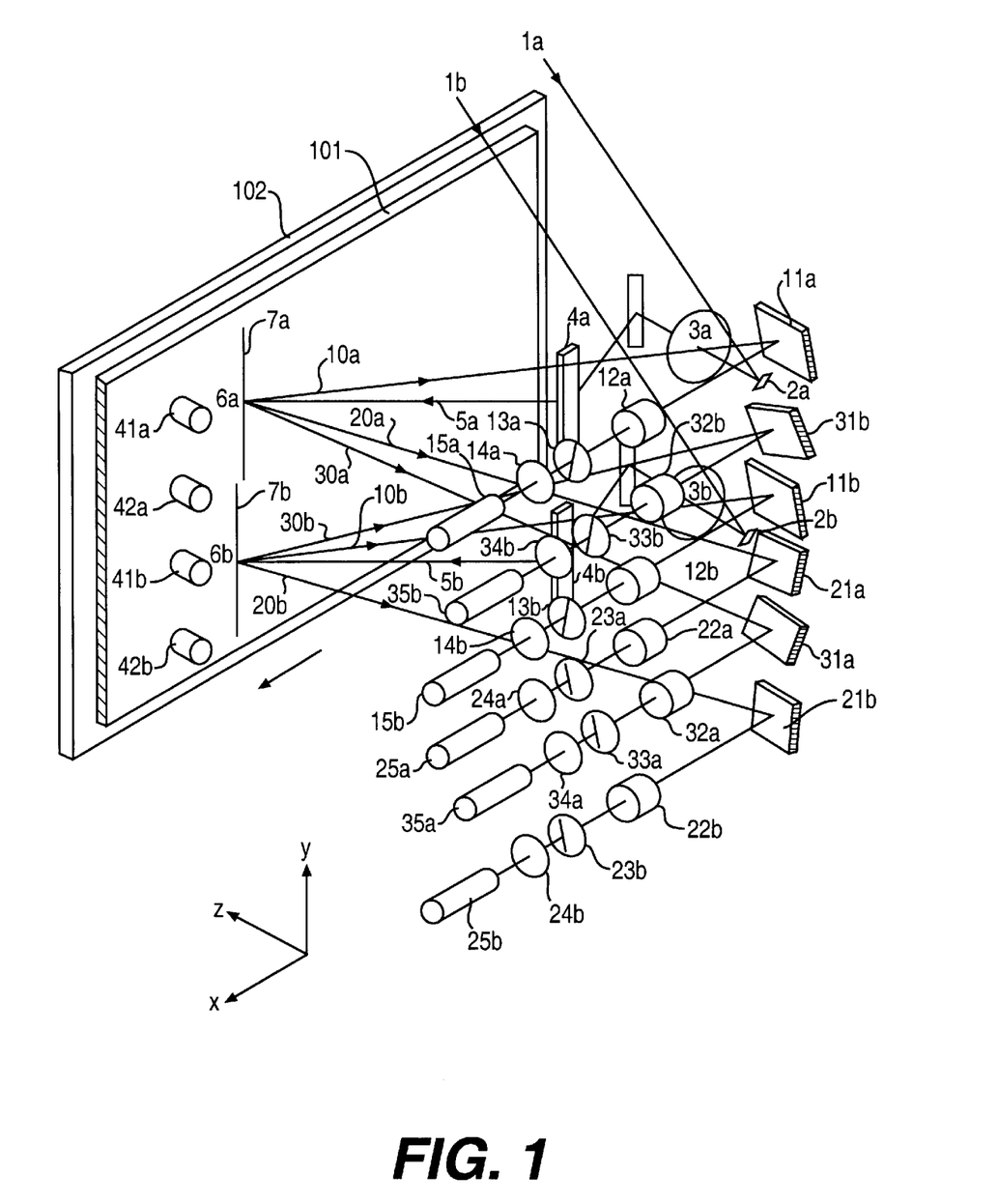
FIG. 1 is a perspective schematic drawing of the configuration of a foreign substance inspecting apparatus according to a first embodiment of the present invention.
Figure 2:
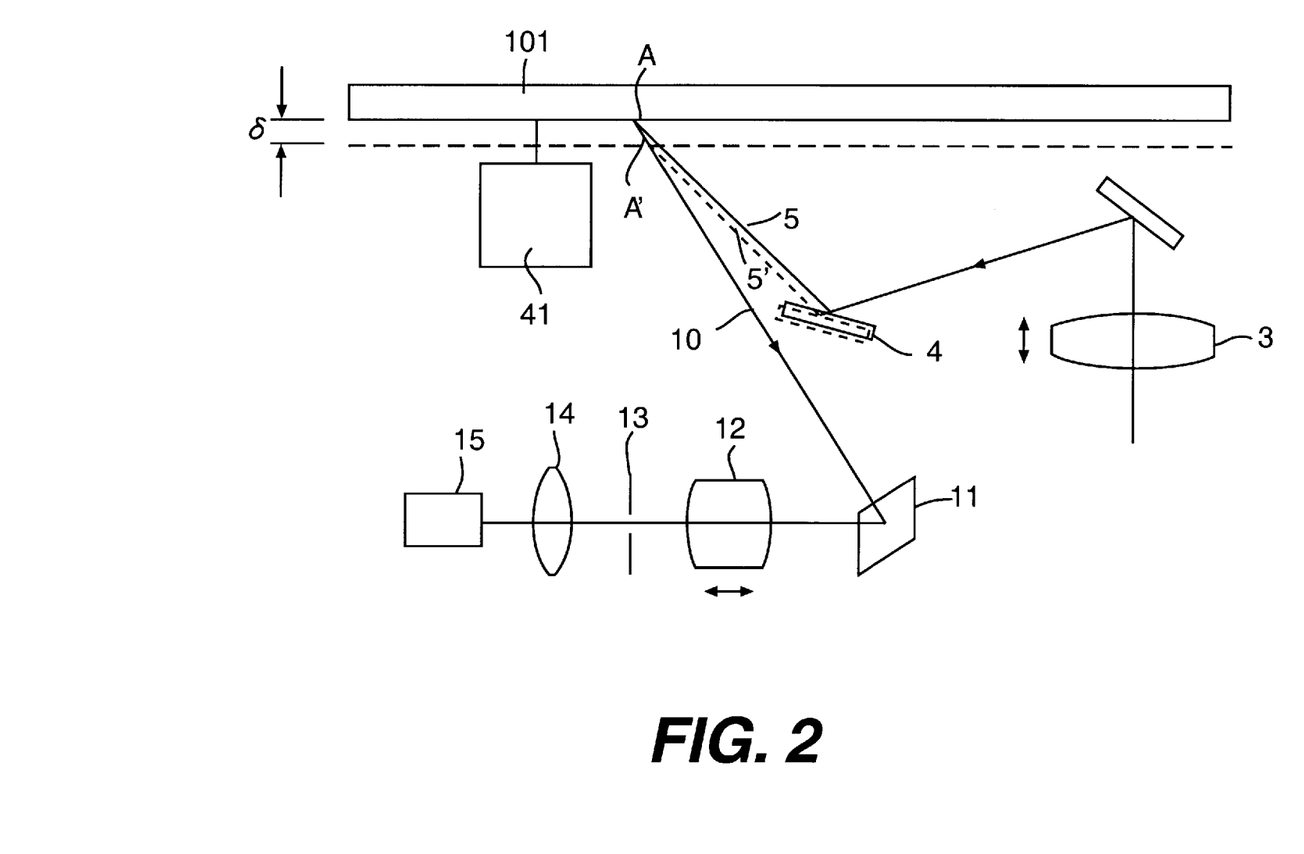
FIG. 2 is a drawing of the apparatus of FIG. 1 to explain the actions for adjusting the focal point of each condensing optical system and the actions for adjusting the position of the beam spot.

A first embodiment of the present invention will now be described with reference to the attached drawings. FIG. 1 is a perspective view schematically showing the configuration of a foreign substance inspecting apparatus according to a first embodiment of the present invention. FIG. 2 is an enlarged planar view showing the configuration of the condensing optical system, the light-receiving optical system and the sensor of FIG. 1.

In FIG. 1, the z-axis is set along the normal direction of the inspected surface of the substrate 101, while the x-axis and y-axis are set along mutually orthogonal directions in the inspected surface of the substrate 101. In addition, in FIG. 2, one condensing optical system, one light-receiving optical system and one sensor are shown representatively. Here, the appended letters (a–c) are omitted from the reference numbers of each constituent element.

In FIG. 1, two mutually parallel beams 1a and 1b, supplied from laser light sources (not shown), are incident on moving mirrors (scanning mirrors) 2a and 2b, respectively. The beam reflected by the moving mirror 2a is collected by a scanning lens 3a and is then incident on a reflective mirror 4a. The reflected beam from the reflective mirror 4a becomes the beam 5a which is obliquely incident on the inspected surface on the substrate 101, such as a large mask or large plate, thereby forming a laser spot 6a. The laser spot 6a is scanned along the y direction on the inspected surface of the substrate 101 by moving the mirror 2a. As a result, a scan locus 7a of the laser spot 6a is formed on the inspected surface of the substrate 101.

Also, the beam reflected by the moving mirror 2b is collected by a scanning lens 3b and is reflected by a reflective mirror 4b. The resulting beam 5b is obliquely incident on the inspected surface on the substrate 101, thereby forming a laser spot 6b. The laser spot 6b is scanned in the y direction of the inspected surface of the substrate 101 by the moving mirror 2b. As a result, a scan locus 7b of the laser spot 6b is formed on the inspected surface of the substrate 101.

As a result, the scanning lens 3a and the reflective mirror 4a form the first condensing optical system for forming the very small laser spot 6a on the inspected surface, and the scanning lens 3b and the reflective mirror 4b form the second condensing optical system for forming the very small laser spot 6b on the inspected surface. In addition, the moving mirror 2a forms the first scanning optical system for causing the laser spot 6a formed by the first condensing optical system to move in the y direction, and the moving mirror 2b forms the second scanning optical system for causing the laser spot 6b formed by the second condensing optical system to move along the y direction.

As shown in FIG. 1, the scanning locus 7a and the scanning locus 7b are separated by a predetermined distance in the x direction while overlapping slightly in the y direction. In addition, the substrate 101 is held on a stage 102 movable in the x direction so that the inspected surface is parallel to the x-y plane. Accordingly, by moving the stage 102 and hence the substrate 101 in the x direction while scanning the two laser spots 6a and 6b in the y direction under the operation of the moving mirrors 2a and 2b, two-dimensional scanning of the inspected surface of the substrate 101 is achieved using the two laser spots 6a and 6b.

When a foreign substance such as very small debris is present in the region on the top side of the inspected surface of the substrate 101 in the drawing, scattered light rays 10a, 20a and 30a from the foreign substance to the laser spot 6a are reflected by reflective mirrors 11a, 21a and 31a, respectively, and are then incident on light-receiving lenses 12a, 22a and 32a, respectively. The scattered light rays 10a, 20a and 30a via the light-receiving lenses 12a, 22a and 32a, respectively, are incident on slit plates 13a, 23a and 33a, respectively, having slit-shaped apertures optically conjugate to the scanning locus 7a. The scattered light rays 10a, 20a and 30a, having passed through the apertures of the slit plates 13a, 23a and 33a, respectively, pass through lenses 14a, 24a and 34a, respectively, and are then received by photoelectric detectors 15a, 25a and 35a arranged at positions conjugate to the diaphragm positions (pupil positions) of the light-receiving receiving lenses 12a, 22a and 32a. In this way, unnecessary light (stray light) other than the scattered light from the foreign substance is blocked by the slit plates 13a, 23a and 33a, and does not reach the photoelectric detectors 15a, 25a and 35a.

Similarly, when a foreign substance such as very small debris is present in the region on the bottom side of the inspected surface of the substrate 101 in the drawing, scattered light rays 10b, 20b and 30b from the foreign substance with respect to the laser spot 6b are received by photoelectric detectors 15b, 25b and 35b, respectively, via reflective mirrors 11b, 21b and 31b, light-receiving lenses 12b, 22b and 32b, slit plates 13b, 23b and 33b and lenses 14b, 24b and 34b, respectively. In addition, the unnecessary light (stray light) other than the scattered light from the foreign substance is blocked by the slit plates 13b, 23b and 33b, and does not reach the photoelectric detectors 15b, 25b and 35b.

In this way, the reflective mirrors 11a, 21a and 31a, the light-receiving lenses 12a, 22a and 32a, the slit plates 13a, 23a and 33a, the lenses 14a, 34a and 34a, and the photoelectric detectors 15a, 25a and 35a form the first through third light-receiving optical systems for receiving the scattered light 10a from the foreign substance with respect to the laser spot 6a formed by the first condensing optical system. In addition, the reflective mirrors 11b, 21b and 31b, the light-receiving lenses 12b, 22b and 32b, the slit plates 13b, 23b and 33b, the lenses 14b, 24b and 34b, and the photoelectric detectors 15b, 25b and 35b form the fourth through sixth light-receiving optical systems for receiving the scattered light 10b from the foreign substance with respect to the laser spot 6b formed by the second condensing optical system.

The intersection between the optical axis of the first through third light-receiving optical systems and the inspected surface of the substrate 101 is configured to be positioned on the scanning locus 7a formed by the first condensing optical system. In addition, the intersection between the optical axis of the fourth through sixth light-receiving optical systems and the inspected surface of the substrate 101 is configured to be positioned on the scanning locus 7b formed by the second condensing optical system.

As described above, the scanning locus 7a and the scanning locus 7b are formed so as to be separated by a predetermined distance in the x direction. Accordingly, scattered light with respect to the laser spot 6a formed by the first condensing optical system is prevented from intermixing with the fourth through sixth light-receiving optical systems, and scattered light with respect to the laser spot 6b formed by the second condensing optical system is prevented from intermixing with the first through third light-receiving optical systems.

However, the scattered light from the foreign substance with respect to the laser spots has weak directivity. Consequently, the scattered light is detected in all of the light-receiving optical systems. On the other hand, the diffracted light from the pattern formed on the inspected surface with respect to the laser light has strong directivity, and is not detected in all of the light-receiving optical systems. In this manner, it is possible to detect a foreign substance on the basis of the output signals from the photoelectric detectors 15a, 25a and 35a, and 15b, 25b and 35b using signal processing technology.

In addition, the foreign substance inspecting apparatus of FIG. 1 has a surface shape measuring system for measuring the surface shape, i.e., the surface position in the z direction of the inspected surface of the substrate 101. In the present embodiment, the surface shape measuring system comprises four sensors 41a, 42a, 41b and 42b arranged in a row in the y direction near the position where the two laser spots 6a and 6b are formed, as shown in FIG. 1. For example, each sensor may be a surface position detection sensor using the oblique incidence method. Thus, the surface shape (the state of undulations and sloping) of the inspected surface of the substrate 101 is measured using the outputs of the sensors 41a, 42a, 41b and 42b. Furthermore, the focus of each condensing optical system may be adjusted according to the measured surface shape, as will be described.

The action of adjusting the focus of each condensing optical system in the foreign substance inspecting apparatus of FIG. 1 and the action of adjusting the positions wherein the laser spots are formed will now be described with reference to FIG. 2.

In FIG. 2, when the inspected surface of the substrate 101 is in the position indicated by the solid lines, the beam collected by the scanning lens 3 is reflected by the reflective mirror 4, becomes beam 5 and forms a laser spot at point A on the inspected surface of the substrate 101. As described above, the point A on the inspected surface is the point of intersection between the inspected surface and the optical axis of the light-receiving optical systems (11–15). Accordingly, the scattered light 10 from the foreign substance with respect to the laser spot formed at point A on the surface of the substrate 101 reaches the photoelectric detector 15 via the reflective mirror 11, the light-receiving lens 12, the slit plate 13 and the lens 14 along the optical axis of the light-receiving optical system.

When the inspected surface near the position where a laser spot is formed moves from the position indicated by the solid lines to the position indicated by the dashed line because of undulations or sloping of the inspected surface of the substrate 101, this displacement δ is measured by a sensor 41. In this manner, by moving the scanning lens 3 along the optical axis thereof by a predetermined amount on the basis of the measured displacement δ, the scanning lens 3 is focused, thereby accomplishing focus adjustment of the condensing optical system.

In addition, by moving the reflective mirror 4 to the position indicated by the dashed lines in the drawing on the basis of the measured displacement δ, the laser spot is formed at the intersection A' between the optical axis of the light-receiving optical system and the inspected surface which has moved. Thus, by merely moving the light-receiving lens 12 along the optical axis without moving the optical axis of the light-receiving optical system, the conjugate relationship is maintained between the aperture of the slit plate 13 and the scanning locus of the laser spot formed at the point A' on the inspected surface of the substrate 101.

That is, unnecessary light, other than the scattered light required for foreign substance detection, is blocked by the slit plate 13, even if the inspected surface varies.

Figure 3:
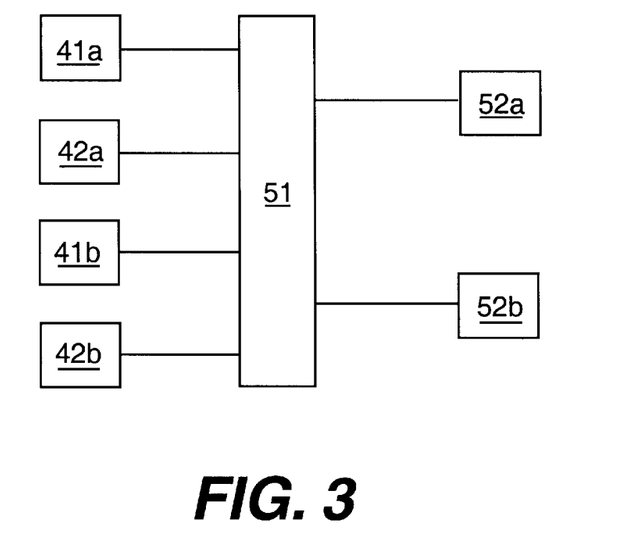
FIG. 3 is a block diagram showing the process to adjust the focal length of each condensing optical system and to adjust the position of the beam spot using the output of the surface shape measuring system.

FIG. 3 is a block diagram showing the process of adjusting the focus of each condensing optical system and adjusting the position where the laser spot is formed according to the output of the surface shape measuring system of FIG. 1.

As shown in FIG. 3, the output of each sensor (41a, 42a, 41b and 42b) is supplied to a computing device 51. In the computing device 51, the shape of the surface near the position where the scanning locus 7a is formed on the inspected surface of the substrate 101 is measured according to the outputs from the sensors 41a and 42a. Thus, the driving amount for the scanning lens 3a necessary to adjust the focus of the first condensing optical system is determined from the information about the shape of the surface near the position where the scanning locus 7a is formed. In addition, the driving amount for the reflective mirror 4a necessary in order to adjust the position where the laser spot 6a is formed is also determined.

In addition, the shape of the surface near the position where the scanning locus 7b is formed in the inspected surface of the substrate 101 is measured from the outputs from the sensors 41b and 42b. Thus, the driving amount for the scanning lens 3b necessary to adjust the focus of the second condensing optical system is determined from the information about the shape of the surface near the position where the scanning locus 7b is formed. In addition, the driving amount for the reflective mirror 4b necessary to adjust the position where the laser spot 6b is formed is also determined.

The information about the required driving amounts for the scanning lens 3a and the reflective mirror 4a found by the computing device 51 is supplied to a driving system 52a (not shown in FIG. 1), and the information about the required driving amounts for the scanning lens 3b and the reflective mirror 4b found by the computing device 51 is supplied to a driving system 52b (not shown in FIG. 1). The driving system 52a drives the scanning lens 3a and the reflective mirror 4a in accordance with the driving amount information that is supplied. In addition, the driving system 52b drives the scanning lens 3b and the reflective mirror 4b in accordance with the driving amount information that is supplied.

Thus, in the present embodiment, two laser spots 6a and 6b are formed on the inspected surface by two condensing optical systems, these two laser spots 6a and 6b scan under the operation of the moving mirrors 2a and 2b, respectively, and form two scanning loci 7a and 7b extending in the y direction. Furthermore, two-dimensional scanning of the inspected surface is achieved using the two laser spots 6a and 6b while causing the inspected surface to be moved in the x direction. Accordingly, the scanning region of the scanning lens 3 of each condensing optical system is made smaller as compared to that of the conventional apparatus which scans the inspected surface using one laser spot formed by one condensing optical system. As a result, the required diameter of each scanning lens can be reduced, thereby realizing reduced production cost of the scanning lens 3 and greater compactness in the apparatus.

In addition, in the present embodiment the shape of the inspected surface is measured by the surface shape measuring system composed of four sensors disposed in the y direction near the two scanning loci 7a and 7b, so that the focus of the scanning lenses 3a and 3b of each condensing optical system is adjusted according to the measured surface shape information. Accordingly, foreign substances are detected with the required detection sensitivity over a large surface even when there is undulation or sloping.

Furthermore, by moving the reflective mirrors 4a and 4b parallel according to the surface shape information measured by the surface shape measuring system, the positions of the laser spots 6a and 6b are adjusted so that each laser spot is formed at the intersection of the inspected surface that has fluctuated and the optical axis of each of the light-receiving optical systems. Thus, the conjugate relationship is maintained between the scanning loci of the laser spots and the apertures of the slit plates (13, 23 and 33) by only moving the light-receiving lenses (12, 22 and 32) along the optical axis without moving the optical axis of each of the light-receiving optical systems. That is, the unnecessary light other than the scattered light required for foreign substance detection is blocked, even if the inspected surface fluctuates. As a result, foreign substances are accurately detected with sufficient detection sensitivity over a large surface.

Figure 4:
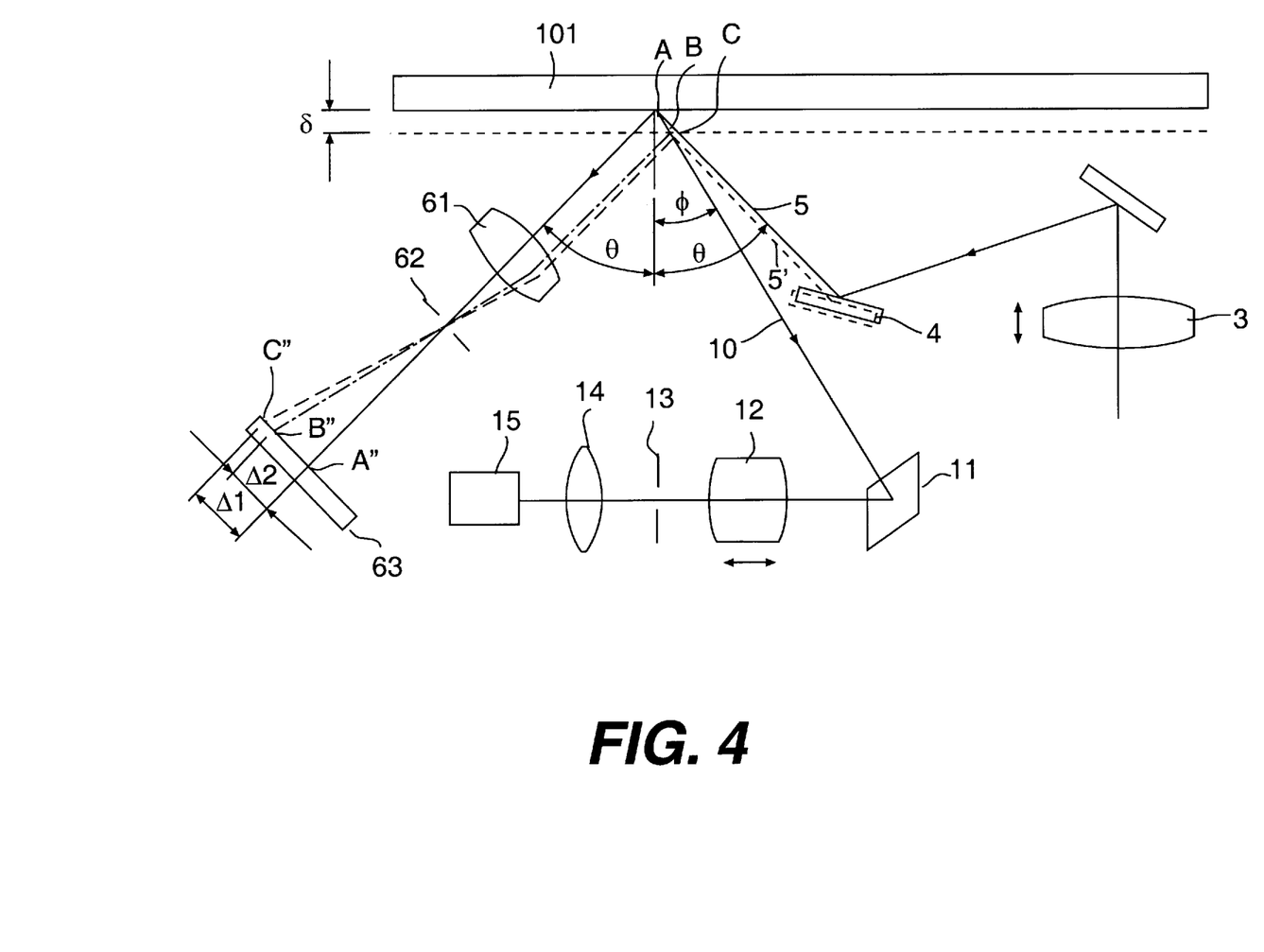
FIG. 4 is a drawing showing another configuration of the surface shape measuring system of FIG. 2.
Figure 5:
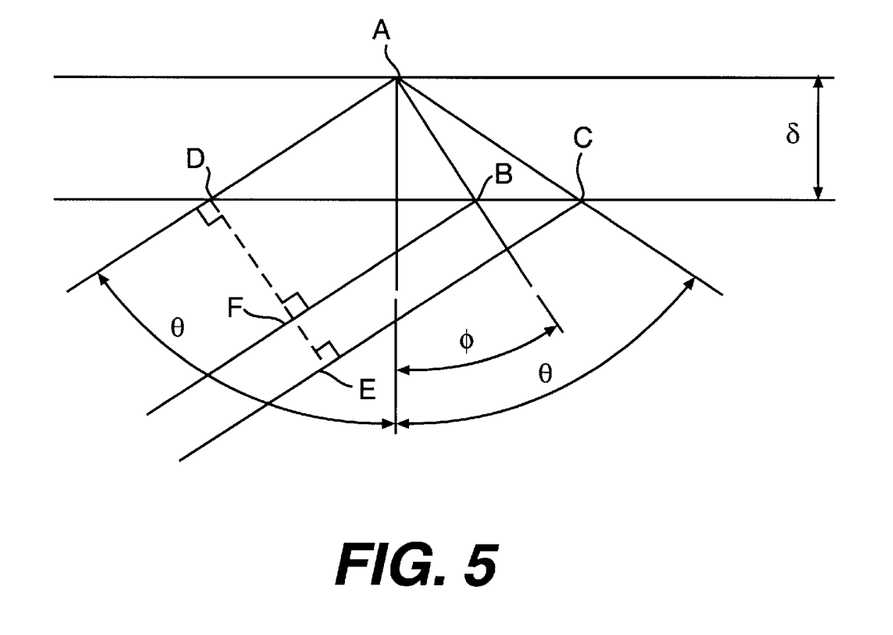
FIG. 5 is an enlargement of a portion of the formation of the beam spot in FIG. 4.

FIG. 4 is a drawing corresponding to FIG. 2 which shows a variation of the surface shape measuring system 41 in FIG. 2. FIG. 5 is a partial enlargement of the laser spot formation position of FIG. 4. In FIG. 4, elements having the same functions as elements in FIG. 2 are labeled with the same reference numbers as in FIG. 2.

In FIG. 4, when the substrate 101 is at the position indicated by the solid lines in the drawing, the beam 5 which is incident on the inspected surface at an angle of incidence $\theta$ via the scanning lens 3 and the reflective mirror 4 forms a laser spot at point A on the inspected surface. The scattered light for a foreign substance with respect to the laser spot is received by the light-receiving optical systems (11–15) having an optical axis forming an angle $\phi$ with respect to the normal line of the inspected surface. On the other hand, the mirror reflected beam of the laser spot passes through a lens 62 and is then incident on an aperture diaphragm 62 positioned at the side focus position. The beam that has passed through the aperture diaphragm forms a laser spot at the point A" on an image sensor 63. Thus, the point A on the inspected surface and the point A" on the image sensor 63 are conjugate via the lens 61.

With reference to FIG. 4 and FIG. 5, when the inspected surface has fluctuated by a distance $\delta$ at the position of laser spot formation, the beam 5 is incident at point C on the inspected surface at an angle of incidence $\theta$. The beam mirror reflected at this point C on the inspected surface passes through the lens 61 and the aperture diaphragm 62 and forms an image of the laser spot at a point C" separated by a distance $\Delta 1$ from the point A" on the image sensor 63. Thus, the displacement $\delta$ of the inspected surface at the position of laser spot formation, and the surface shape of the inspected surface, can be measured from the displacement $\Delta 1$ of the image of the laser spot. In this case, it is preferable for the scanning lens 3 to be telecentric on the image side (the substrate 101 side). The characteristic of the surface shape measuring system shown in the variation in FIG. 4 is that it is possible to accomplish surface shape measuring continuously along the scanning loci of the laser spots within the effective field of the lens 61.

However, as described with reference to FIG. 2, when adjustment of the position of laser spot formation is accomplished through parallel movement of the reflective mirror 4, if the inspected surface varies by a distance $\delta$, the beam 5 is incident on the point B on the inspected surface at the angle of incidence $\theta$. The beam mirror reflected at the point B on the inspected surface passes through the lens 61 and the diaphragm aperture 62 and forms an image of the laser spot at the point B" separated by the distance Δ2 from the point A" on the image sensor 63. That is, the displacement of the image of the laser spot changes because of the influence of adjustment of the position of laser spot formation.

The change in the amount of movement of the laser spot caused by adjustment of the position of laser spot formation will now be examined.

In FIG. 5, the distance DE between the optical axis AD (the path of the beam reflected at point A on the surface being inspected) of the surface shape measuring system (61–63) of FIG. 4 and the path CE of the beam mirror reflected at the point C on the inspected surface when the inspected surface of the substrate 101 has fluctuated downward by a distance δ is expressed as:

$$DE = 2\delta \tan\theta \cos\theta = 2\delta \sin\theta \tag{1}$$

In addition, when the magnification of the light-receiving optical system (11–15) is designated β, the displacement Δ1 of the image of the laser spot accompanying fluctuation in the inspected surface is expressed as:

$$\Delta 1 = DE\beta = 2\beta\delta \tan\theta \cos\theta \tag{2}$$

Next, when the beam is incident with an angle of incidence θ at the point B on the inspected surface through parallel movement of the reflective mirror 4, the distance DF between the path BF of the beam mirror reflected at the point B and the optical axis AD of the surface shape measuring system (61–63) is expressed as:

$$DF = \delta(\tan\theta + \tan\phi)\cos\theta \tag{3}$$

Also, the displacement Δ2 of the image of the laser spot accompanying fluctuations in the position of laser spot formation and fluctuations in the surface being inspected is expressed as:

$$\Delta 2 = DF\,\beta = \beta\delta(\tan\theta + \tan\phi)\cos\theta \tag{4}$$

The change in the displacement, Δ1−Δ2, of the images of the laser spot caused by fluctuations in the position of laser spot formation is expressed as:

$$\Delta 1 - \Delta 2 = \beta\delta \cos\theta(\tan\theta - \tan\phi) \tag{5}$$

Thus, the fluctuation amount δ of the surface being inspected is found from equation (2) by the surface shape measuring system (61–63), and the displacement of the reflective mirror 4 and the scanning lens 3 is determined from fluctuation amount δ of the inspected surface. Hence, the position of laser spot is adjusted by parallel movement of the reflective mirror 4, and the focus of the condensing optical system is adjusted by the motion of the scanning lens 3. In addition, it is possible to control the displacement of the reflective mirror 4 from equation (5) using the surface shape measuring system (61–63).

As concrete examples of numerical values, it is possible to rewrite the above-described equations (2) and (5) as equations (6) and (7) below when the angle of incidence θ (that is to say, the angle formed by the optical axis of the condensing optical system and the normal line of the surface being inspected) of the beam on the surface being inspected is 45° and the angle formed between the optical axis of the light-receiving optical system and the normal line to the inspected surface is 35°.

$$\Delta 1 = 1.4\,\beta\delta \tag{6}$$

$$\Delta 1 - \Delta 2 = 0.2\,\beta\delta \tag{7}$$

With reference to equations (6) and (7), the change Δ1−Δ2 in the displacement of the image of the laser spot accompanying parallel movement of the reflective mirror 4 is around ⅐ the displacement Δ1 of the image of the laser spot accompanying fluctuations in the inspected surface. Thus, in a normal configuration, the effects of fluctuation in the position of laser spot formation in measuring the surface shape may be ignored because the change Δ1−Δ2 in the displacement of the image of the laser spot caused by fluctuations in the position of laser spot formation is sufficiently small as compared to the displacement Δ1 of the image of the laser spot accompanying the fluctuations in the inspected surface.

In the above-described embodiment, an example has been described wherein two laser spots are formed using two condensing optical systems. However, a predetermined number of laser spots may be formed using a predetermined number of condensing optical systems in accordance with the size of the inspected surface.

As described above, with the first embodiment, a plurality of very small light spots are formed on the inspected surface by a plurality of condensing optical systems. Consequently, the required diameter of the scanning lens of each condensing optical system is reduced and it is possible to reduce production costs for the scanning lenses and to obtain a compact apparatus. In addition, with the first embodiment, the focus of each condensing optical system is adjusted separately in accordance with the surface shape of the inspected surface. Consequently, foreign substances are detected with the required detection sensitivity over the entirety of a large inspected surface.

Next, a second embodiment of the present invention will be described.

In the second embodiment a plurality of light spots are formed on the inspected surface by a plurality of scanning optical systems, and the inspected surface is scanned by the plurality of light spots formed. Furthermore, the scattered light from the foreign substance with respect to each light spot is received by each light-receiving optical system, and the foreign substance is detected on the basis of the scattered light received. Thus, a plurality of light spots are formed on the inspected surface by a plurality of scanning optical systems. Further, the necessary scanning region of each scanning optical system for a large inspected surface is reduced. As a result, the required diameter of the scanning lenses of each scanning optical system and the required diameter of the light-receiving lenses of each light-receiving optical system become smaller, and a reduction in production costs is achieved for scanning lenses and light-receiving lenses in a more compact apparatus.

In addition, with the second embodiment, the mirror reflected light of each light spot is absorbed by the operation of a light-absorbing member composed of an organic material that absorbs light having a specific wavelength, such as acrylic resin. The light-absorbing member formed of acrylic resin is less expensive, lighter in weight, and more rigid than the conventional light-absorbing member formed of glass. Accordingly, all of the mirror reflected light from the entire scanning range may be absorbed with one light-absorbing member formed integrally without providing an adhesion unit. As a result, the creation of noise from the scattering in the mirror reflected light at the adhesion unit of the conventional glass member is suppressed, thereby allowing the detection of foreign substances with high accuracy.

Figure 6:
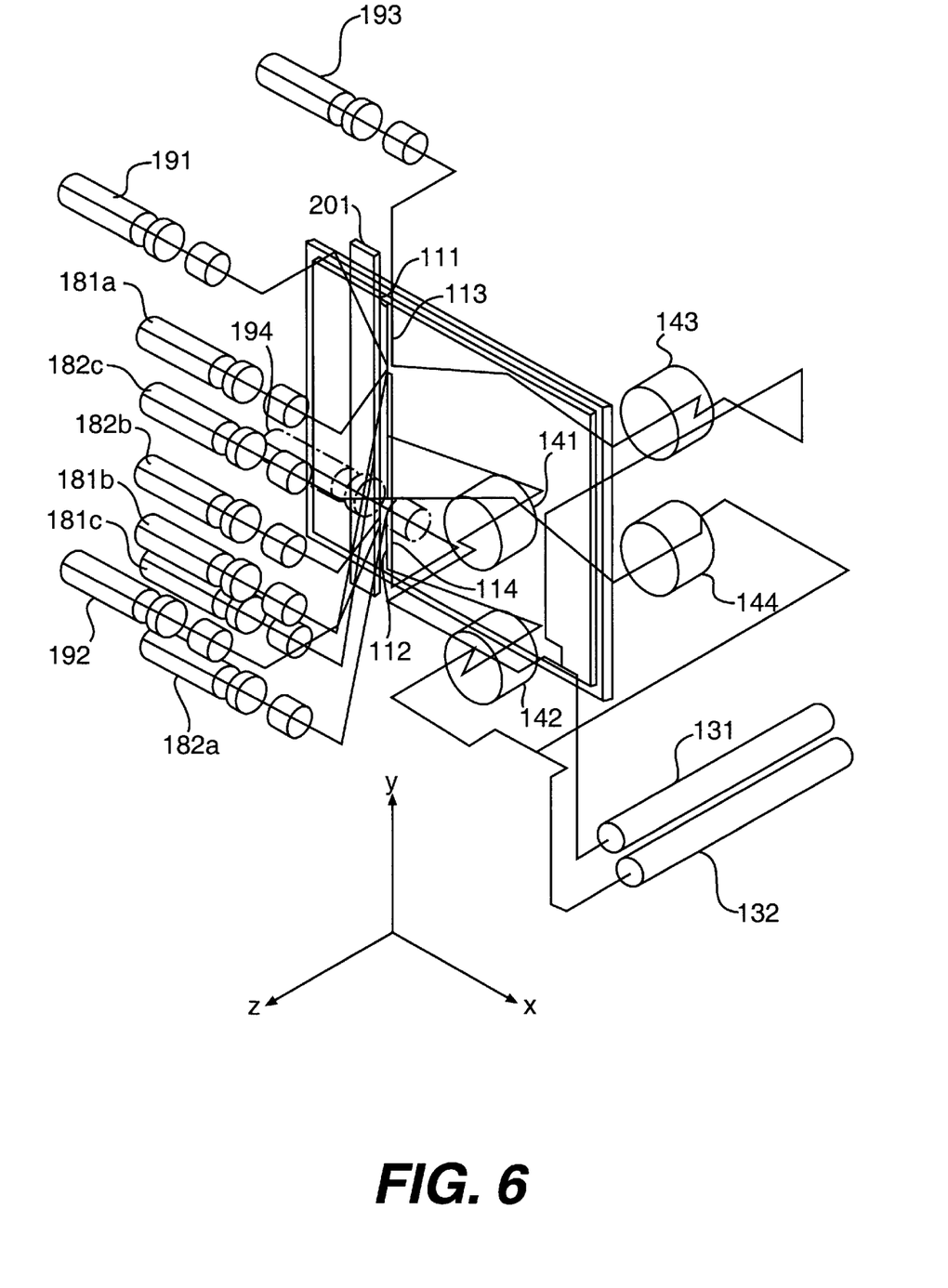
FIG. 6 is an perspective schematic drawing of the configuration of a foreign substance inspecting apparatus according to a second embodiment of the present invention.

A second embodiment of the present invention will now be described with reference to the attached drawings. FIG. 6 is a perspective drawing schematically showing the configuration of a foreign substance inspecting apparatus. In addition, FIG. 7 is a perspective drawing showing an enlargement of the configuration of the scanning optical system and the light-receiving optical system according for one scanning locus 111 of the plurality of scanning loci in FIG. 6.

Figure 7:
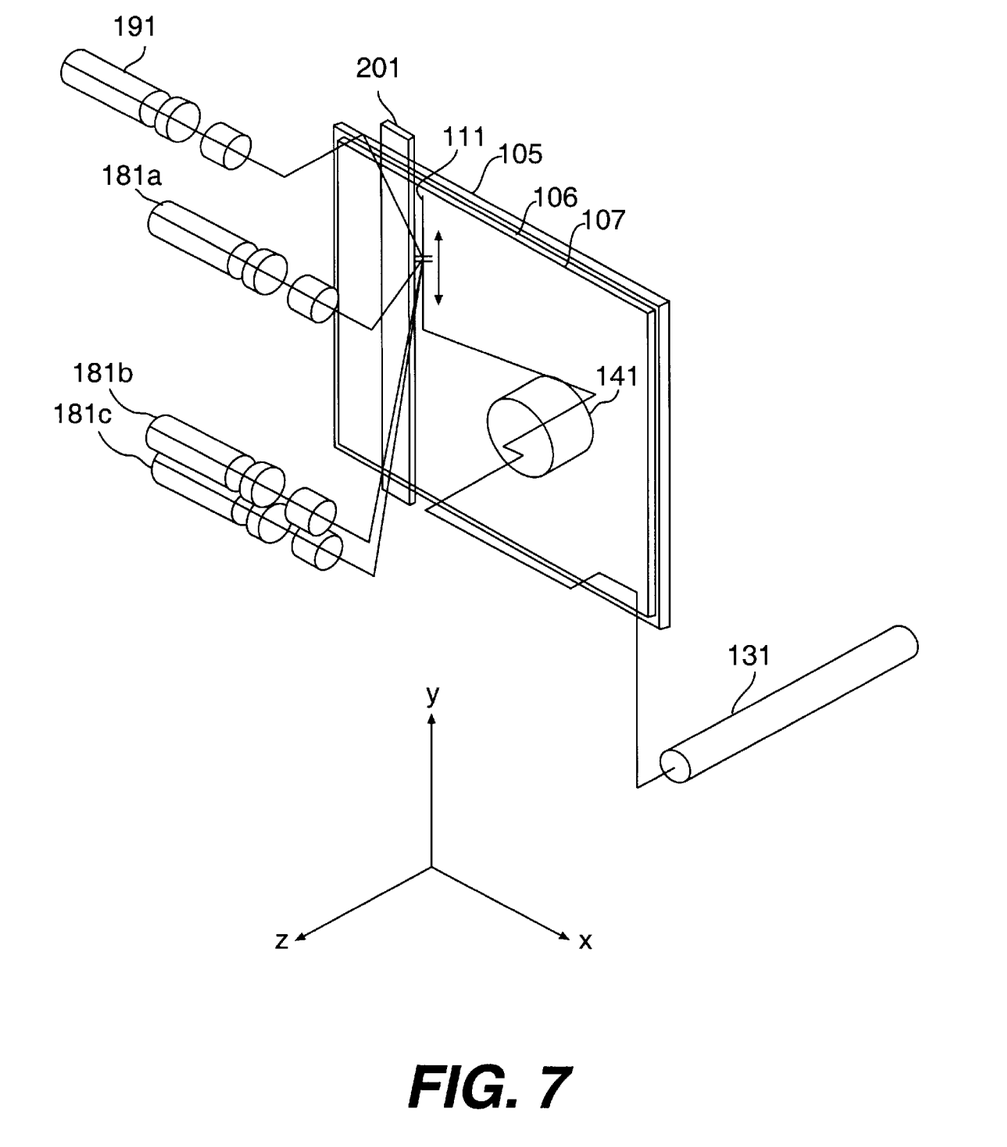
FIG. 7 is an enlargement of the scanning optical system and light-receiving optical system in the scanning locus of the apparatus of FIG. 6.

In FIGS. 6 and 7, the z axis is set along the direction normal to the pattern surface 106 of the mask 105, and the x axis and the y axis are set along mutually orthogonal directions in the pattern surface 106. In addition, drawings of the deflecting devices such as bending mirrors are omitted in FIGS. 6 and 7 for clarity.

In the present embodiment, the apparatus is applied to a mask on which a pellicle membrane is stretched. Accordingly, the inspected surfaces in the present embodiment are the surface on which the pattern of the mask is formed, i.e., the pattern surface; the surface on which the pattern of the mask is not formed, i.e., the glass surface; and the surface that does not face the mask pattern surface out of the pellicle membrane surfaces, i.e., the pellicle surface. However, as described below, a scanning locus (scanning range) is formed on the pattern surface and the pellicle surface by a common optical system.

First, the beam emitted from a laser light source 131 is expanded by a beam expander (not shown), and is then incident on a scanning lens 141 via a moving mirror (not shown). The beam collected by the scanning lens 141 is obliquely incident on the pellicle surface 107 and the pattern surface 106 of the mask 105, and forms a laser spot. The laser spot formed on the pellicle surface 107 and the pattern surface 106 is scanned along the y direction under the operation of the moving mirror. As a result, a scanning locus 111 of the laser spot is formed on the pellicle surface 107 and the pattern surface 106. Thus, the laser light source 131, the moving mirror and the scanning lens 141 form a scanning optical system that creates the scanning locus 111 on the pellicle surface 107 and the pattern surface 106, which are the inspected surfaces.

On the other hand, the beam emitted from a laser light source 132 is expanded by a beam expander (not shown), and is then incident on a scanning lens 142 via a moving mirror (not shown). The beam collected by the scanning lens 142 is obliquely incident on the pellicle surface 107 and the pattern surface 106 of the mask 105, and forms a laser spot. The laser spot formed on the pellicle surface 107 and the pattern surface 106 is scanned in the y direction under the operation of the moving mirror. As a result, a scanning locus 112 of the laser spot is formed on the pellicle surface 107 and the pattern surface 106. Thus, the laser light source 132, the moving mirror, and the scanning lens 142 form a scanning optical system that creates the scanning locus 112 on the pellicle surface 107 and the pattern surface 106, which are the inspected surfaces.

In addition, the beam emitted from a laser light source 131 is expanded by a beam expander (not shown), and is then incident on a scanning lens 143 via a moving mirror (not shown). The beam collected by the scanning lens 143 is obliquely incident on the glass surface of the mask 105, and forms a laser spot. The laser spot formed on the glass surface of the mask 105 is scanned in the y direction under the operation of the moving mirror. As a result, a scanning locus 113 of the laser spot is formed on the glass surface of the mask 105. Thus, the laser light source 131, the moving mirror, and the scanning lens 143 form a scanning optical system that creates the scanning locus 113 on the glass surface, which is the inspected surface.

Furthermore, the beam emitted from a laser light source 132 is expanded by a beam expander (not shown), and is then incident on a scanning lens 144 via a moving mirror (not shown). The beam collected by the scanning lens 144 is obliquely incident on the glass surface of the mask 105, and forms a laser spot. The laser spot formed on the glass surface of the mask 105 is scanned in the y direction under the operation of the moving mirror. As a result, a scanning locus 1 14 of the laser spot is formed on the glass surface of the mask 105. Thus, the laser light source 132, the moving mirror and the scanning lens 144 form a scanning optical system that creates the scanning locus 114 on the glass surface, which is the inspected surface.

The mask 105 is supported on a stage (not shown) capable of moving in the x direction so that the pattern on the mask is parallel to the x-y plane. In addition, the scanning locus 111 and the scanning locus 112 are formed continuously in the y direction over the entirety of each inspected region of the pattern surface 106 and the pellicle surface 107. Furthermore, the scanning locus 113 and the scanning locus 114 are formed continuously in the y direction over the entirety of the scanned region or the glass surface of the mask 105.

Accordingly, by moving the stage and hence the mask 105 in the x direction while scanning the laser spots in the y direction under the operation of the moving mirrors, the entirety of each inspected region of the pattern surface 106 and the pellicle surface 107 is scanned using the two scanning loci 1 1 and 1 12, and the entirety of the inspected regions of the glass surface of the mask 105 is scanned using the two scanning loci 113 and 114.

When a foreign substance, such as very small debris, is present on the pattern surface 106 of the mask 105, the scattered light from the foreign substance with respect to the laser spot forming the scanning locus 111 is received by the light-receiving optical systems 181a–181c for the pattern surface. In addition, when a foreign substance, such as very small debris, is present on the pellicle surface 107, the scattered light from the foreign substance with respect to the laser spot forming the scanning locus 111 is received by the light-receiving optical system 191 for the pellicle surface. Similarly, the scattered light from the foreign substance with respect to the laser spot forming the scanning locus 112 is received by the light-receiving optical systems 182a–182c for the pattern surface and the light-receiving optical system 192 for the pellicle surface.

Also, when a foreign substance, such as very small debris, is present on the glass surface of the mask 105, the scattered light from the foreign substance with respect to the laser spot forming the scanning locus 113 is received by the light-receiving optical systems 181a–181c for the glass surface. In addition, the scattered light from the foreign substance with respect to the laser spot forming the scanning locus 114 is received by one light-receiving optical system 194 for the glass surface.

Thus, the light-receiving optical systems corresponding to the scanning locus 111 are the light-receiving optical systems 181a–181c for the pattern surface and the light-receiving optical system 191 for the pellicle surface. In addition, the light-receiving optical systems corresponding to the scanning locus 112 are the light-receiving optical systems 182a–182c for the pattern surface and the light-receiving optical system 192 for the pellicle surface. Furthermore, the light-receiving optical system corresponding to the scanning locus 113 is the light-receiving optical system 193 for the glass surface, and the light-receiving optical system corresponding to the scanning locus 114 is the light-receiving optical system 194 for the glass surface. Each of the light-receiving optical systems has a built-in photoelectron multiplier device such as a photomultiplier.

However, the mirror reflected light obliquely incident on the pattern surface 106 and the pellicle surface 107 of the mask via the scanning lens 141 and the scanning lens 142, respectively, is absorbed by a light-absorbing member 201 made of acrylic resin. The light-absorbing member 201 is a plate member integrally formed extending parallel to the pattern surface 106 in the y direction, for example. The dimensions and arrangement are determined so that all of the mirror reflected light created in the scanning loci 111 and 112 is incident thereon. In addition, the mirror reflected light of the beams obliquely incident on the glass surface of the mask 105 via the scanning lens 143 and the scanning lens 144 is absorbed by a separate light-absorbing member (not shown) having the same function as the above light-absorbing member 201.

As described above, each light-receiving optical system has a built-in photoelectric multiplier device such as a photomultiplier. Accordingly, each light-receiving optical system outputs a photoelectric signal according to the intensity of the scattered light received. Thus, a foreign substance adhered to the pellicle surface 107 is detected from the output signals of the light-receiving optical systems 191 and 192 for the pellicle surface, through signal processing. In addition, a foreign substance adhered to the pattern surface 106 of the mask 105 is detected from the output signals of the light-receiving optical systems 181a–181c and 182a–182c for the pattern surface. Furthermore, a foreign substance adhered to the glass surface of the mask 105 is detected from the output signals of the light-receiving optical systems 193 and 194 for the glass surface.

In this manner, with the present embodiment two scanning loci 111 and 112 are formed by two scanning optical systems on the pattern surface 106 and the pellicle surface 107, respectively, which are the inspected surfaces. In addition, two scanning loci 113 and 114 are formed by two scanning optical systems on the glass surface, which is the inspected surface. Furthermore, the laser spots are scanned two-dimensionally over the entire inspected region of each inspected surface by moving the mask 105 and hence the inspected surface in the x direction. Furthermore, the scattered light from a foreign substance with respect to each laser spot is received by each light-receiving optical system, and the foreign substance is detected on the basis of the scattered light received. Accordingly, the field region of the light-receiving lens of each light-receiving optical system and the scanning region of the scanning lens of each scanning optical system reduced as compared to that of the conventional apparatus that scans each inspected surface using only one laser spot formed by one scanning optical system. As a result, the required diameter of each scanning lens and each light-receiving lens is reduced, thereby realizing a reduction in production costs and size of the apparatus.

Figure 8A:
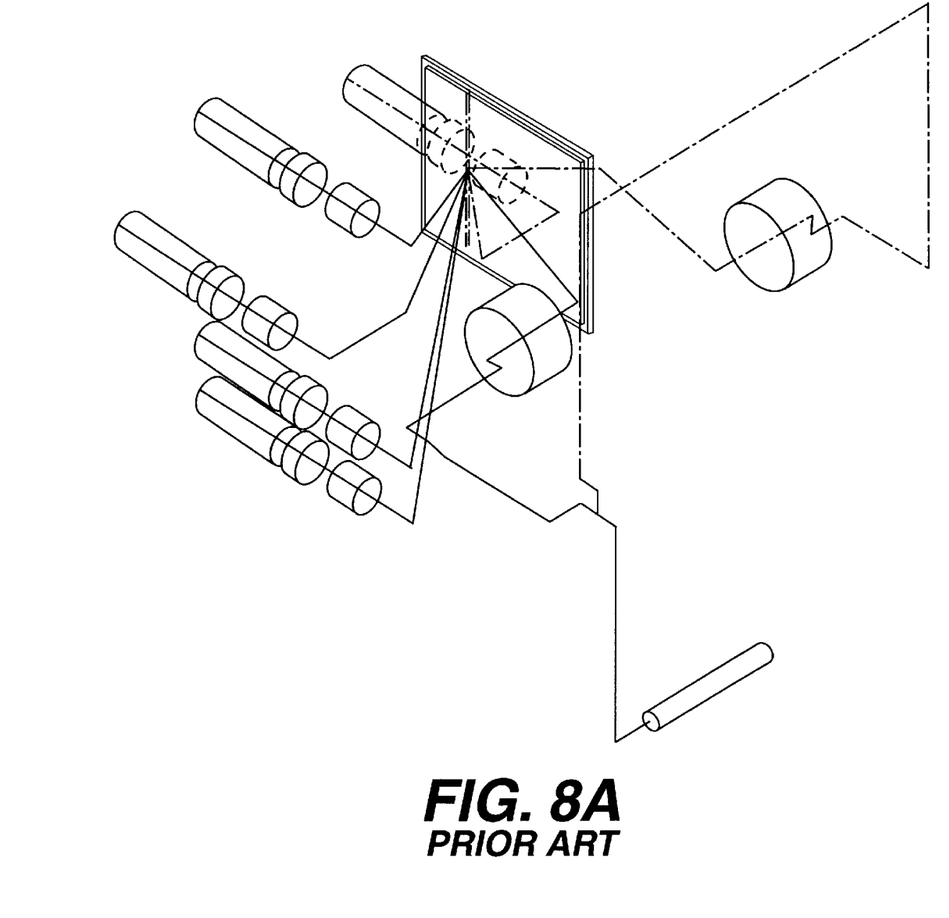
FIG. 8A is a drawing showing the configuration of a conventional apparatus for scanning the inspected surface using one laser spot formed by one scanning optical system.
Figure 8B:
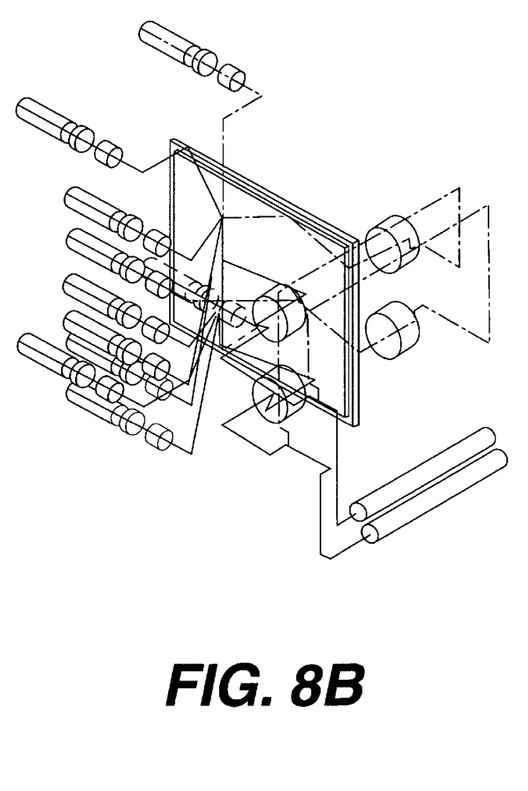
FIG. 8B is a drawing showing the configuration of the apparatus according to the second embodiment for scanning each inspected surface with two laser spots formed by two scanning optical systems.

FIGS. 8A and 8B show the efficacy of greater compactness in the apparatus shown in FIG. 6. Specifically, FIG. 8A shows the configuration of a conventional apparatus for scanning the inspected surface using one laser spot formed by one scanning optical system, and FIG. 8B shows the entire configuration of the apparatus of the present embodiment that scans each inspected surface using two laser spots formed by two scanning optical systems. In FIGS. 8A and 8B, the conventional apparatus and the apparatus of the present embodiment ate compared following a standard design premise, but it is clear that the efficacy of the greater compactness in the apparatus the present invention is striking.

Figure 9:
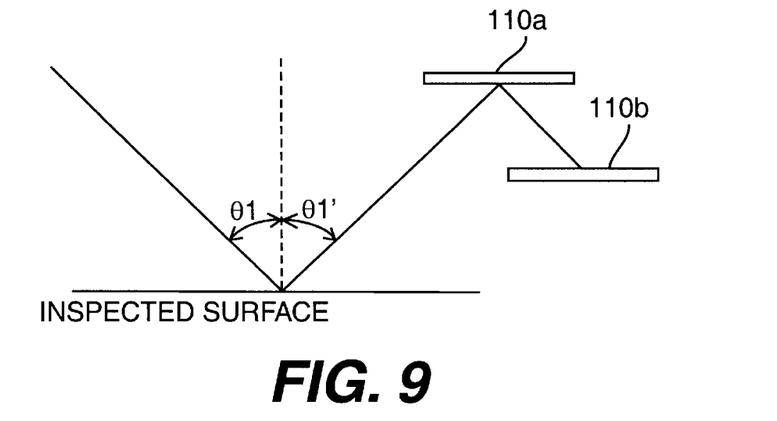
FIGS. 9 to 11 show other configurations of the light-absorbing member of FIGS. 6 and 7.
Figure 10:
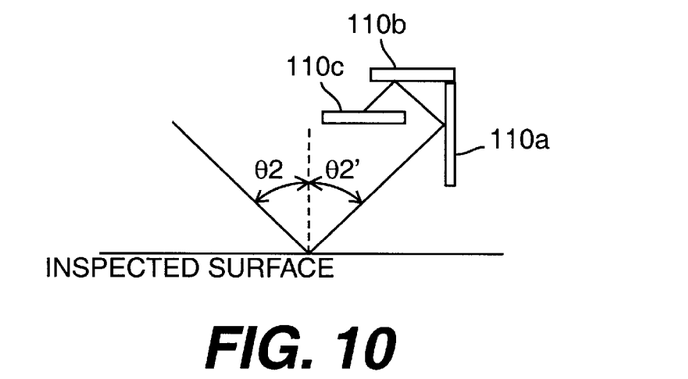
Figure 11:
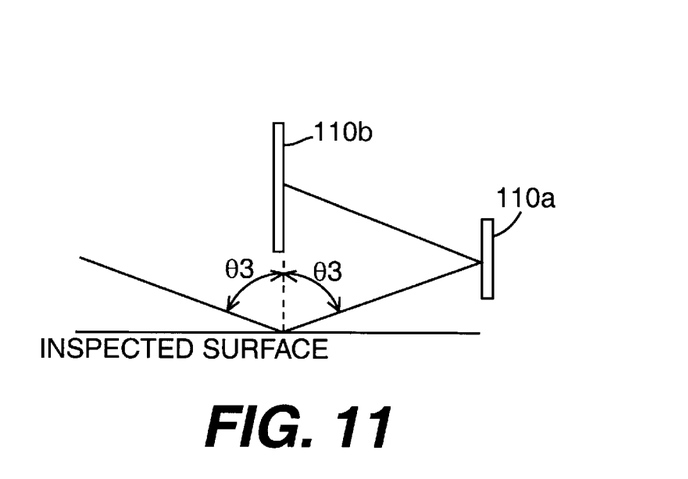

FIGS. 9 to 11 show other configurations of the light-absorbing member in FIGS. 6 and 7.

In the configuration of FIG. 9, the beam incident at an angle of incidence θ1 with respect to the inspected surface is mirror reflected at an angle of reflection θ1'(θ1'=−θ1) in the inspected surface, and is then incident on a first light-absorbing member 110a positioned parallel to the inspected surface. Furthermore, the beam mirror reflected without being absorbed by the first light-absorbing member 110a is incident on a second light-absorbing member 110b positioned parallel to the inspected surface. The first light-absorbing member 110a and the second light-absorbing member 110b are made of an acrylic resin the same as the light-absorbing member 201 in FIGS. 6 and 7. Thus, in the configuration of FIG. 9, all of the mirror reflected beam from the inspected surface is absorbed by the first light-absorbing member 110a and the second light-absorbing member 110b. As a result, it is possible to achieve a greater absorption efficacy than with the embodiment of FIGS. 6 and 7 which accomplishes absorption of the mirror reflected beam from the inspected surface using one light-absorbing member 201.

In the configuration of FIG. 10, the beam incident at an angle of incidence θ2 with respect to the inspected surface is mirror reflected at an angle of reflection θ2'(θ2'=−θ2) in the inspected surface, and is then incident on a first light-absorbing member 110a positioned perpendicular to the inspected surface. The beam mirror reflected without being absorbed by the first light-absorbing member 110a is incident on the second light-absorbing member 110b position parallel to the inspected surface. Furthermore, the beam mirror reflected without being absorbed by the second light-absorbing member 110b is incident on a third light-absorbing member 110c position parallel with the inspected surface. Thus, in the configuration of FIG. 10, all of the mirror reflected beam from the inspected surface is absorbed by the first through third light-absorbing members 110a–110c.

In the configuration of FIG. 11, the beam incident at an angle of incidence θ3 with respect to the inspected surface is mirror reflected at an angle of reflection θ3'(θ3'=−θ3) in the inspected surface, and is then incident on the first light-absorbing member 110a positioned perpendicular to the inspected surface. Furthermore, the beam mirror reflected without being absorbed by the first light-absorbing member 110a is incident on the second light-absorbing member 110b position perpendicular to the inspected surface. Thus, in the variation in FIG. 11, all of the mirror reflected beam from the inspected surface is absorbed by the first light-absorbing member 110a and the second light-absorbing member 110b.

In the above-described embodiment, an example was shown wherein two scanning loci are formed on the inspected surface using two scanning optical systems, but it is also possible to form a predetermined number of scanning loci using a predetermined number of scanning optical systems in accordance with the size of the inspected surface. In addition, a light-absorbing member made of acrylic resin was used, but the light-absorbing member may be made of an organic material that absorbs light having a specific wavelength, such as polycarbonate, or an organic material with a pigment which absorbs light having a specific wavelength.

As described above, with the second embodiment, a plurality of light spots are formed on the inspected surface using a plurality of scanning optical systems and the scattered light from a foreign substance with respect to each light spot is received by each light-receiving optical system. Consequently, it is possible to realize a reduction in production costs and size of the apparatus. In addition, signal noise caused by scattering in the mirror reflected light at the adhesion unit of a conventional glass member is suppressed through the operation of light-absorbing members made of acrylic resin, thereby obtaining highly accurate detection of foreign substances.

It will be apparent to those skilled in the art that various modifications and variations can be made in the foreign substance inspecting apparatus of the present invention without departing from the spirit or scope of the invention. Thus, it is intended that the present invention cover the modifications and variations of this invention provided they come within the scope of the appended claims and their equivalents.

What is claimed is:

1. A foreign substance inspecting apparatus for detecting a foreign substance on a surface, comprising:

a light source for providing light;

a plurality of condensing optical systems for collecting the light from the light source and for forming a plurality of light spots on the surface;

a scanning system for scanning the surface using the light spots formed by the condensing optical systems;

a detecting optical system for detecting light scattered from at least one of the light spots by the foreign substance on the surface; and a surface shape measuring system for measuring a shape of the surface, wherein a focus of each one of the condensing optical systems is individually adjusted according to the surface shape measured by the surface shape measuring system.

2. The foreign substance inspecting apparatus according to claim 1, wherein the scanning system includes a plurality of scanning optical systems for forming a plurality of scanning loci by moving each one of the plurality of light spots formed by the plurality of condensing optical systems in a first direction and includes means for moving the inspected surface in a second direction, the second direction being orthogonal to the first direction.

3. The foreign substance inspecting apparatus according to claim 2, wherein the detecting optical system includes a plurality of light-receiving optical systems for receiving the light scattered from the light spots by the foreign substance on the surface.

4. The foreign substance inspecting apparatus according to claim 2, wherein the scanning loci of the light spots in the first direction are mutually separated in the second direction by the plurality of scanning optical systems.

5. The foreign substance inspecting apparatus according to claim 2, wherein each one of the plurality of scanning optical systems includes a moving mirror provided in the optical path between the light source and a corresponding one of the plurality of condensing optical systems.

6. The foreign substance inspecting apparatus according to claim 2, further comprising a bending mirror disposed in each optical path between the surface and a respective one of the plurality of condensing optical systems, and wherein each of the bending mirrors are moved parallel so that the intersections between the surface and the optical axis of each of the plurality of light-receiving optical systems are positioned on a respective one of the plurality of scanning loci.

7. The foreign substance inspecting apparatus according to claim 1, wherein the detecting optical system has a plurality of light-receiving optical systems for receiving the light scattered from the light spots by the foreign substance on the surface.

8. The foreign substance inspecting apparatus according to claim 1, wherein the surface shape measuring system has a light-receiving system for receiving the mirror reflected light of at least one light spot of the plurality of light spots, and measures the surface position of the surface according to the light-receiving position of the mirror reflected light.

9. The foreign substance inspecting apparatus according to claim 1, further comprising a light absorbing member for absorbing mirror reflected light from the light spots.

10. A method for detecting the presence of a foreign substance on a surface, comprising the steps of:

providing light from a light source;

collecting the light from the light source using a plurality of condensing optical systems;

forming a plurality of light spots on the surface from the light collected by the plurality of condensing optical systems;

scanning the surface using the light spots formed by the condensing optical systems;

detecting light scattered by the foreign substance on the surface from at least one of the light spots;

measuring a shape of the surface; and individually adjusting a focus of each one of the condensing optical systems according to the measured surface shape.

11. The method according to claim 10, wherein the step of scanning the surface includes the steps of forming a plurality of scanning loci by moving each one of the plurality of light spots formed by the plurality of condensing optical systems in a first direction and moving the inspected surface in a second direction, the second direction being orthogonal to the first direction.

12. The method according to claim 11, wherein in the step of forming the scanning loci the scanning loci are mutually separated in the second direction.

13. The method according to claim 11, wherein the step of forming the scanning loci includes the step of moving a mirror disposed in the optical path between the light source and a corresponding one of the plurality of condensing optical systems.

14. The method according to claim 11, further comprising the step of moving a plurality of bending mirrors parallel so that the intersections between the surface and the optical axis of each of the plurality of light-receiving optical systems are positioned on a respective one of the plurality of the scanning loci, each one of the plurality of bending mirrors disposed in an optical path between the surface and a respective one of the plurality of condensing optical systems.

15. The method according to claim 10, wherein in the light detecting step light scattered from the light spots is received by a plurality of light-receiving optical systems.

16. The foreign substance inspecting apparatus according to claim 10, wherein the step of measuring the surface shape includes the steps of receiving mirror reflected light of at least one light spot of the plurality of light spots and measuring the surface position of the surface according to the light-receiving position of the mirror reflected light.

17. The method according to claim 16, further comprising the step of absorbing mirror reflected light from the light spots.

* * * * *